US008501453B2

(12) United States Patent
Walbeck

(10) Patent No.: US 8,501,453 B2
(45) Date of Patent: Aug. 6, 2013

(54) METHODS FOR DRYING BACTERIOPHAGE AND BACTERIOPHAGE-CONTAINING COMPOSITIONS, THE RESULTING DRY COMPOSITIONS, AND METHODS OF USE

(75) Inventor: Alan K. Walbeck, Sandy, UT (US)

(73) Assignee: Omnilytics, Incorporated, Salt Lake City, UT (US)

( * ) Notice: Subject to any disclaimer, the term of this patent is extended or adjusted under 35 U.S.C. 154(b) by 616 days.

(21) Appl. No.: 12/243,865

(22) Filed: Oct. 1, 2008

(65) Prior Publication Data
US 2009/0093041 A1    Apr. 9, 2009

Related U.S. Application Data

(60) Provisional application No. 60/976,727, filed on Oct. 1, 2007.

(51) Int. Cl.
*C12N 7/00* (2006.01)
(52) U.S. Cl.
USPC ...................................................... 435/235.1
(58) Field of Classification Search
None
See application file for complete search history.

(56) References Cited

U.S. PATENT DOCUMENTS

| 5,149,653 A | 9/1992 | Roser |
| 5,792,625 A | 8/1998 | Klaenhammer et al. |
| 5,842,289 A * | 12/1998 | Chandran et al. ............... 34/579 |
| 7,601,347 B2 * | 10/2009 | Waddell et al. ............. 424/93.6 |
| 2003/0234012 A1 | 12/2003 | Bosteels |
| 2005/0050759 A1 | 3/2005 | Chandran et al. |

FOREIGN PATENT DOCUMENTS

WO    03000274 A2    1/2003

OTHER PUBLICATIONS

Chopin, M.C., Journal of Dairy Science, 1980, vol. 47, p. 131-139.*
Zbicinski et al. "Pulse combustion: an advanced technology for efficient drying" 2002, 12 pages.*
Wang et al., Improvement of the Dissolution Rate of Nitrendipine Using a New Pulse Combustion Drying Method, Chem. Pharm. Bull., Aug. 2007, pp. 1119-1125, vol. 55.
PCT International Search Report for Application PCT/US08/78494 dated Dec. 5, 2008.

* cited by examiner

*Primary Examiner* — Kade Ariani
(74) *Attorney, Agent, or Firm* — Durham Jones & Pinegar Intellectual Property Law Group

(57) ABSTRACT

Liquid bacteriophage products may be dried to form dry bacteriophage products. Drying may be effected by pulse combustion drying processes. When dried, the number of viable bacteriophage particles is reduced by no more than about two log ($10^2$). The resulting dry bacteriophage product, therefore includes at least one percent of the number of viable bacteriophage particles that were present in the original liquid bacteriophage product.

21 Claims, 3 Drawing Sheets

METHODS FOR DRYING BACTERIOPHAGE AND BACTERIOPHAGE-CONTAINING COMPOSITIONS, THE RESULTING DRY COMPOSITIONS, AND METHODS OF USE

PRIORITY CLAIM

A claim for priority is made to U.S. Provisional Patent Application Ser. No. 60/976,727, filed on Oct. 1, 2007, the entire disclosure of which is hereby incorporated herein by this reference.

FIELD OF INVENTION

The present invention relates generally to methods for drying bacteriophage and compositions that include bacteriophage. More specifically, the present invention relates to use of pulse combustion atomization spray drying processes to spray dry bacteriophage and bacteriophage-containing compositions. The present invention also includes dry compositions that include bacteriophage, as well as to methods for using dry compositions that include bacteriophage.

BACKGROUND OF RELATED ART

Bacteriophage may be produced using fermentation processes, in which liquid fermentation media, bacterial hosts, and bacteriophage are mixed with one another and incubated. Liquid lysate mixtures that include bacterial debris, fermentation media and an increased concentration bacteriophage result from such fermentation processes. In producing bacteriophage, the nature of the lysate and the interaction with the lysed host must be considered. Bacteriophage thrive within the fermentation environment, and typically continue to exist within that lysate for extended periods of time (with limited exceptions). If the bacteriophage is removed from the liquid lysate, or the environment is changed slightly, the viability of the bacteriophage could be compromised.

Additionally, liquids, such as water, promote the desired random interaction between bacteriophage and the targeted bacterial host. Accordingly, bacteriophage is typically applied in liquid form to substrates (e.g., plants, meats, etc.) that may be contaminated or infected with specific target bacteria.

As such, typically, liquid lysate solutions that result from bacteriophage fermentation processes are merely clarified to produce a final bacteriophage product, which is then shipped without further modification.

There are, however, situations where it would be more desirable to supply a dry bacteriophage product or a more compact (e.g., concentrated, etc.) bacteriophage product. An example of such a situation is when a host bacteria excretes a particular enzyme, protease, toxin, or other by-product that may harm the bacteriophage over time; e.g., by breaking down protein (which are the building blocks of bacteriophage), leading to the eventual demise of bacteriophage that remains within the liquid lysate solution (clarified or not). This breakdown occurs over time, even after the bacterial hosts have been killed by the bacteriophage, and can occur in as little as a few hours or as long as many days or even weeks. As a result, the production of liquid bacteriophage products has been limited to "well-behaved" bacterial hosts (those which do not excrete by-products that could harm the bacteriophage), which may limit the types or concentrations of certain types of bacteriophage that can be effectively produced on an industrial scale.

While various attempts have been made to produce dry bacteriophage products, including lyophilization (i.e., freeze-drying) and spray drying processes, the susceptibility of bacteriophage particles to the conditions (e.g., temperatures, shear forces, etc.) of such processes have rendered these attempts largely unsuccessful, "killing" or otherwise diminishing the virulence of the vast majority of the bacteriophage particles. In fact, conventional spray dry processes typically result in products with at least a five log ($10^5$) to eight log ($10^8$) reduction in bacteriophage efficacy, representing a reduction in the effectiveness of the final product, compared to its pre-dried liquid form, of 99.999% to 99.999999%.

There are needs for bacteriophage and bacteriophage-containing compositions that are in dry (e.g., powder, granules, etc.) form, for methods for drying bacteriophage and bacteriophage-containing compositions, and for methods for using dry bacteriophage and dry compositions that include bacteriophage.

SUMMARY

Bacteriophage are sensitive to shearing forces, extremely high temperatures (including the amount of time the bacteriophage is exposed to high temperatures) and other environmental variables. Due to the sensitive nature of bacteriophage, care may be taken to avoid damaging the anatomy of this microorganism. Of particular concern is keeping the portions of the bacteriophage requisite for adsorption, such as the tail fibers, intact. If these portions of the bacteriophage anatomy do not remain intact or viable, the bacteriophage will not be able to make contact and adsorb to the walls of the targeted bacteria strain.

The present invention, in one aspect, includes processes for converting a liquid bacteriophage product to a dry or a substantially dry bacteriophage product. In various embodiments, such processes may include, but are not necessarily limited to, evaporation, lyophilization, spray drying, and a subset of spray drying that is known in the art as "pulse combustion drying." These processes may, of course, be modified or tailored to maintain the efficacy and virulence of bacteriophage particles. Such processes are effected in a manner that reduces the number of viable bacteriophage particles, from processed liquid bacteriophage product to dry bacteriophage product, by no more than about two log ($10^2$) and, in some embodiments, by no more than about one log ($10^1$). In other embodiments, little (e.g., about 25% or less) or no reduction in the number of viable, or virulent, phage particles may occur. When liquid is added to the resulting dry bacteriophage product to reconstitute it to its original volume, the reconstituted liquid bacteriophage product may include at least $10^7$ plaque forming units (pfu) per milliliter (ml) and, in some embodiments, at least $10^8$ pfu/ml.

In another aspect, the present invention includes dry bacteriophage products, which comprises, and may consist essentially of, bacteriophage and a carrier material, and may additionally include bacterial debris and residual fermentation media. A dry bacteriophage product according to the present invention includes at least one percent of the number of viable bacteriophage particles that were present in the liquid solution from which the dry bacteriophage product was produced, and may include at least ten percent of the number of viable bacteriophage particles that were present in the liquid solution from which the dry bacteriophage product was produced. In some embodiments, a dry bacteriophage product of the present invention, when reconstituted to its pre-dried concentration, may include at least about $10^7$ pfu/ml and, in more specific embodiments, include at least $10^8$ pfu/ml.

The present invention also includes methods for using dry bacteriophage products and/or compositions including dry bacteriophage product to control bacterial populations. In some embodiments of such methods, a dry bacteriophage product may be reconstituted in a liquid (e.g., water, etc.), then applied to a substrate. In other embodiments, such a composition may be applied in dry form, where liquid that is already present on the substrate, is concurrently applied to the substrate, or that subsequently appears on the substrate (e.g., by application, condensation, etc.) facilitates exposure of the bacteriophage to target bacteria.

Other aspects, as well as features and advantages, of the present invention will become apparent to those of skill in the art through consideration of the ensuing description and the appended claims.

BRIEF DESCRIPTION OF THE DRAWINGS

In the drawings:

FIG. 1 is a table showing process parameters and results of a rotary atomization study; and FIGS. 2A and 2B are tables showing process parameters and results of various pulse combustion drying tests.

DETAILED DESCRIPTION

Figure 2A:
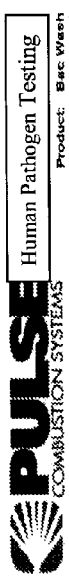

The present invention includes methods for forming dry bacteriophage products from liquid bacteriophage products, such as fermentation mixtures that include bacteriophage and, optionally, fermentation media, bacterial hosts for the bacteriophage, and/or bacterial debris, or "lysate." In such a method, a bulk liquid preparation including the bacteriophage (i.e., an industrial-scale quantity, which may be measured in gallons or liters) may be dried in fewer than ten hours and, in some embodiments, a few liters of liquid bacteriophage product (e.g., up to about twenty liters) can be dried in as quickly as about thirty minutes, twenty minutes, or even ten minutes or less. Thus, drying may be effected at a rate of about one liter every minute and a half, about one liter per minute, or even two liters per minute.

The present invention includes methods for forming dry bacteriophage products from liquid bacteriophage products, such as fermentation mixtures that include bacteriophage and, optionally, fermentation media, bacterial hosts for the bacteriophage, and/or bacterial debris, or "lysate." In such a method, a bulk liquid preparation including the bacteriophage (i.e., an industrial-scale quantity, which may be measured in gallons or liters) may be dried in fewer than ten hours and, in some embodiments, a few liters of liquid bacteriophage product (e.g., up to about twenty liters) can be dried in as quickly as about thirty minutes, twenty minutes, or even ten minutes or less. Thus, drying may be effected at a rate of about one liter every minute and a half, about one liter per minute, or even two liters per minute.

When methods for forming dry bacteriophage products in accordance with teachings of the present invention are employed, the viability of a liquid bacteriophage product, or its virulence (i.e., the ability of bacteriophage to infect a host bacteria), is substantially maintained during the drying process. As an example, in some embodiments, the dry bacteriophage product that results from a drying process of the present invention may reduce the number of viable, or virulent, bacteriophage particles to no less than ten percent (10%) of the number of viable, or virulent, bacteriophage particles that were present in the initial, liquid bacteriophage product, representing no more than a one log ($10^1$) reduction in viable, or virulent, bacteriophage particles. In some embodiments, a two log ($10^2$) reduction of viable, or virulent, bacteriophage particles may be acceptable, with the resulting dry bacteriophage product including at least one percent (1%) of the viable, or virulent, bacteriophage particles that were present in the initial, liquid bacteriophage product. In other embodiments, the reduction in viable phage particles may be as small as about 25% or less, with about 75% or more of the phage particles retaining their viability throughout the drying process.

As noted above, due to the delicate nature of bacteriophage (e.g., their tail fibers or other areas that are needed for the bacteriophage to effectively adsorb to a targeted host microorganism), the conditions (e.g., shear forces, temperatures, etc.) of conventional drying processes (e.g., conventional lyophilization, conventional spray drying, etc.) have rendered previous attempts to form dry bacteriophage products with acceptable levels of viable, or virulent bacteriophage particles unsuccessful.

In fact, initial attempts to convert liquid bacteriophage products to dry bacteriophage products were unsuccessful, as evidenced by the following example.

Example 1

Spray drying processes convert bulk liquid into a spray or fine mist, which eventually becomes a fine powder through the combined use of pressurized air and heat. The conversion of a bulk liquid into a spray or fine mist may be effected through a process called "atomization." Atomization can be performed through a variety of known techniques. Examples of such techniques include atomization through high-pressure nozzles and rotary atomization.

Nozzle atomization systems generate the highest shearing forces, which start at a very high pressure feed pump, then channel the bulk liquid feed through a high precision orifice. Once the fine mist is safely injected through the orifice, the mist is heated. The mixing of the small droplets with the heat is a relatively slow process with a nozzle system, as is resulting transfer of heat to the droplet.

In rotary atomization systems, the pressures that are required and the shearing forces that are applied to a bulk liquid are greatly reduced from those used in nozzle atomization systems. Due to the complex atomization process, the number of moving parts increases slightly and repair costs are slightly higher. Overall, it was believed that rotary atomization would provide the best solution for drying bulk liquid bacteriophage product.

A rotary atomization study was performed using a PRODUCTION MINOR™ rotary atomization spray dryer, available from GEO Niro of Søborg, Denmark. Liquid bacteriophage products (i.e., fermentation products that included bacteriophage, fermentation media, and bacterial debris, or lysate) that included three different types of bacteriophage were used, each effective in controlling a different bacterial host: (1) bacteriophage effective against *Clavibacter michiganensis* pv. *michiganensis*, a plant pathogen (causes Canker on tomato plants); (2) bacteriophage effective against *Xanthomonas campestris* pv. *vesicatoria*, a plant pathogen (causes Spot on tomato and pepper plants); and (3) bacteriophage effective against *Escherichia coli* O157:H7, a human pathogen (causes sickness and death among humans). In an effort to optimize the recovery of viable, or virulent, bacteriophage, the rotary atomization spray dryer was set to its lowest possible inlet and outlet temperature settings.

Figure 1:
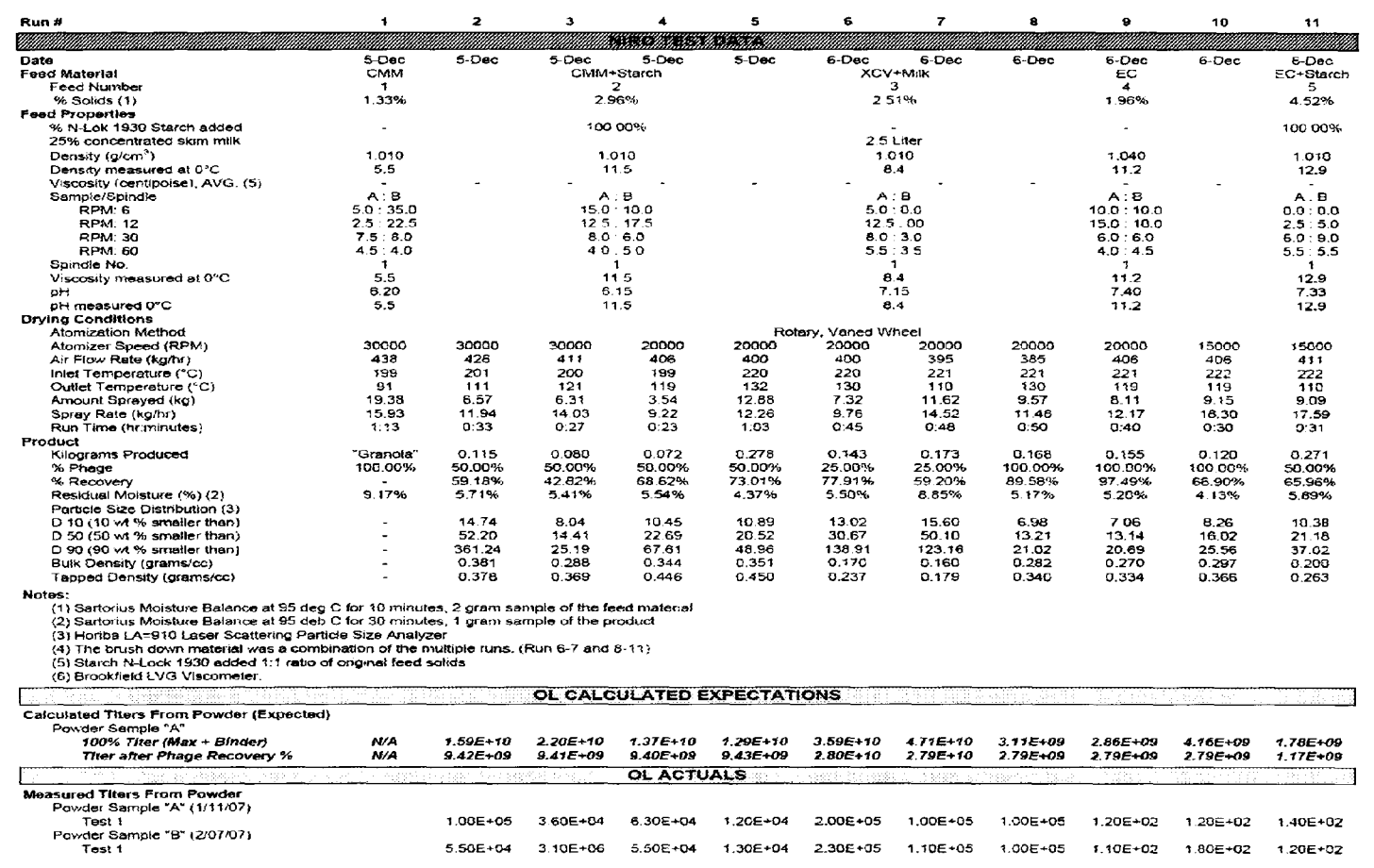

The process parameters and results are set forth in the table of FIG. 1.

The predicted recovery rates of the dry bacteriophage product (a powder) for controlling the two plant pathogens were in the range of $1.29 \times 10^{10}$ pfu/ml (low) to $4.71 \times 10^{10}$ pfu/ml (high). Actual results were observed to be in the range of $1.20 \times 10^4$ pfu/ml (low) to $3.1 \times 10^6$ pfu/ml, or a 4 to 6 log reduction in viable, or virulent, bacteriophage. The bacteriophage effective against human pathogens faired even worse, with predicted recovery rates of the dry bacteriophage product in the range of $1.17 \times 10^9$ pfu/ml (low) to $4.16 \times 10^9$ pfu/ml (high) and actual results observed in the range of $1.10 \times 10^2$ pfu/ml (low) to $1.80 \times 10^2$ pfu/ml, representing a 7+ log reduction in viable, or virulent, bacteriophage. It should be noted that the most optimal process conditions were applied, and still the results were extremely disappointing.

Despite the high expectations for rotary spray drying processes and their subsequent and significant failure, another study was conducted to determine whether or not an acceptable dry bacteriophage product could be produced. In that study, pulse combustion drying processes, were used.

Pulse combustion drying may be effected in a manner that virtually eliminates any possible shear.

In some embodiments, the percent solids content of the liquid bacteriophage product may be increased before the liquid bacteriophage product is subjected to drying processes. For example, a carrier material may be pre-dissolved or otherwise mixed into the liquid bacteriophage product. Without limiting the scope of the present invention, the carrier material may include dried milk (e.g., nonfat powdered milk, etc.), trehalose, maltodextrin, or the like.

Known gas dynamic atomization techniques may be used with an extremely low feed pressure (e.g., about 1 psi); i.e., the pressure at which a liquid bacteriophage product is introduced into a pulse combustion drying apparatus. In some embodiments, low feed pressure may be achieved by introducing the liquid bacteriophage product into the pulse combustion drying apparatus through an open pipe, rather than through a precision orifice or wheel, to a dryer.

In the drying process, droplets of the liquid bacteriophage product were nearly instantaneously exposed to heat.

By tailoring one or more of the type of carrier material, amount of carrier material, feed pump speed/pressure, combustion pressure (e.g., about 0.10 bar, etc.), contact temperature (e.g., about 540° C. or less, etc.), exit temperature (e.g., about 82° C. or less, etc.), and the amount of time a liquid bacteriophage product and/or a dry bacteriophage product is exposed to an increased temperature, an environment can be created where bacteriophage recovery (i.e., viability, virulence, etc.) percentages are extremely high.

Example 2

In a study using pulse combustion drying, a fantastic discovery was made: bacteriophage recovery percentages were extremely high when compared with other techniques, including recovery percentages of about 1% or more, recovery percentages of about 10% or more, and, in some cases, up to 100% recovery was observed, thus highlighting the viability of pulse combustion drying as a technique for forming dry bacteriophage products.

Again, in this study, two of the three different types of liquid bacteriophage products (i.e., fermentation products that included bacteriophage, fermentation media, and bacterial debris, or lysate) used in the previous study were repeated here: (1) bacteriophage effective against *Xanthomonas campestris* pv. *vesicatoria*, a plant pathogen (causes Spot on tomato and pepper plants); and (2) bacteriophage effective against *Escherichia coli* O157:H7, a human pathogen (causes sickness and death among humans). The solids contents of the liquid bacteriophage products were increased by the addition of carrier materials.

Figure 2B:
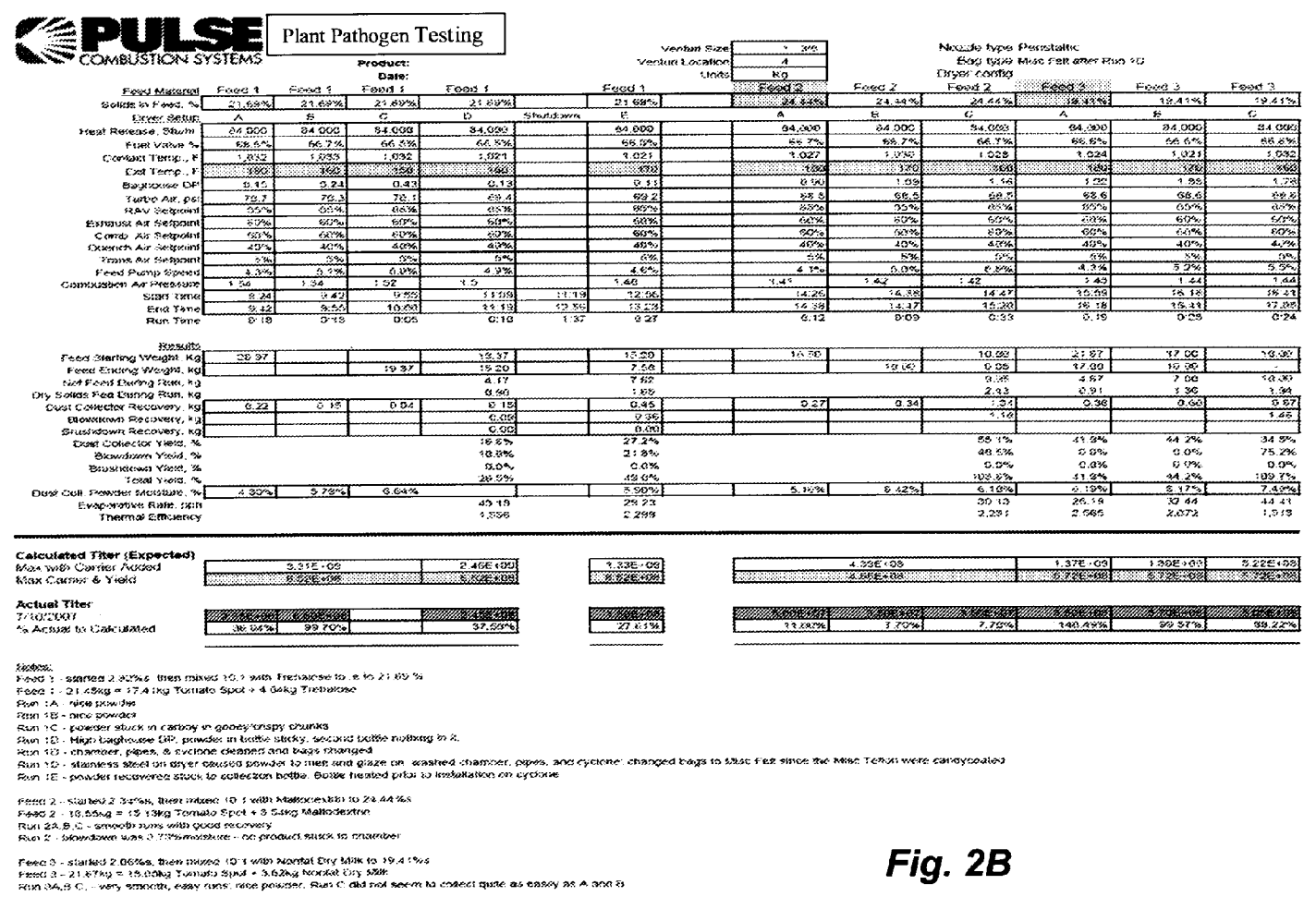

The tables of FIGS. 2A and 2B set forth the process parameters and results of various pulse combustion drying tests, which were effected by a pulse combustion dryer available from Pulse Combustion Systems of Payson, Ariz., in which liquid bacteriophage products were converted to dry bacteriophage products.

The predicted recovery rates of the dry powder (from the bacteriophage used to control the plant pathogen) were in the range of $4.55 \times 10^8$ pfu/ml (low) to $6.52 \times 10^8$ pfu/ml (high). Actual results were observed to be in the range of $3.50 \times 10^7$ pfu/ml (low) to $8.50 \times 10^8$ pfu/ml, or less than one log ($10^1$) reduction in viable, or virulent, bacteriophage in all cases, and within titering error (within 50%) in most cases. The bacteriophage effective against human pathogens produced similar results with predicted recovery rates of the dry powder in the range of $1.83 \times 10^8$ pfu/ml (low) to $1.98 \times 10^8$ pfu/ml (high) and actual results observed in the range of $1.50 \times 10^7$ pfu/ml (low) to $1.40 \times 10^8$ pfu/ml, again a one log ($10^1$) or less reduction in viable bacteriophage in all cases, and within titering error (within 50%) in many cases.

In various embodiments, the present invention includes the production of a highly effective dry bacteriophage product (e.g., in powder form) from a liquid bacteriophage product, which may comprise any combination of fermentation media, magnesium sulfate, lysate, bacteria, deionized, distilled or filtered tap water, lysozyme, DNAse, RNAse, and antifoaming agents, or through the manipulation of the described bacteriophage liquid through the addition of chemicals such as KOH or NaOH for the purposes of adjusting pH. In some embodiments, an optional carrier material (such as dried milk, trehalose, maltodextrin or the like) may be included in order to increase the percent solid content of the original feed material, while maintaining viability of the final powder. This can potentially increase the percentage of solids in the feed from a low percentage (e.g., 5% or less) to a much higher percentage (e.g., 20% or more). Embodiments in which no carrier material is used, or in which different types of carrier materials are used, are, of course, also within the scope of the present invention.

Embodiments of the present invention include, but are not limited to, use of bacteriophage lysate including bacteriophage effective against human pathogens, animal pathogens, plant pathogens, or non-pathogenic strains of bacteria. This includes, but is not limited to, bacteriophage that are effective against one or more of the following plant pathogens: *Xanthomonas, Pseudomonas, Clavibacter, Ralstonia, Acidovorax, Erwinia, Burkholderia, Agrobacterium, Bacillus*, etc. It also includes, but is not limited to, bacteriophage that are effective against one or more of the following human pathogens: *Escherichia coli* O157:H7, *Salmonella, Clostridium, Campylobacter, Listeria, Streptococcus, Staphylococcus, Helicobacter, Propionibacterium*, etc.

In some embodiments, spray drying processes, including, but not limited to, pulse combustion drying processes, may be used. An effective spray drying process may, in some embodiments, employ minimal shearing forces, employ relatively low overall temperatures, and/or minimize the amount of time a liquid bacteriophage product is exposed to an increased temperature. These processes may be conducted in relatively short periods of time (e.g., less than ten hours, about two hours or less, about one hour or less) while substantially maintaining the viability, or virulence, of bacteriophage particles from the bulk liquid bacteriophage product (e.g., the dry bacteriophage product has at least one percent, at least ten percent, etc., of the viability, or virulence, of the bulk liquid bacteriophage product).

In other embodiments, when teachings of the present invention are applied, liquid bacteriophage product may be converted to a dry bacteriophage product by way of lyophilization processes.

In addition to drying processes and the dry bacteriophage products resulting from such processes, the present invention includes methods of using dry bacteriophage and/or dry bacteriophage-containing compositions. In some embodiments, a dry bacteriophage product may be diluted into a liquid media prior to, during, or following application of the dry powder to a substrate. The movement of bacteriophage is random, as they exhibit no mechanism for motility. As a crop protectant or in food safety applications, typical fluid dispersion methods may involve application of the product via pressurized spray systems, in which case the dry powder is previously dissolved within the liquid solution.

In animal, including human, applications, the bacteriophage may be applied either through direct ingestions (in which case the product is dissolved within the stomach or digestive system) or applied topically via a liquid, gel or lotion.

Although the foregoing description includes many specifics, these should not be construed as limiting the scope of the present invention but, merely, as providing illustrations of some of the presently preferred embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions and modifications to the invention as disclosed herein which fall within the meaning and scope of the claims are to be embraced thereby.

What is claimed:

1. A method for manufacturing a dry bacteriophage preparation, comprising subjecting a bulk liquid bacteriophage product comprising a number of viable bacteriophage particles to pulse combustion drying to form a dry bacteriophage product, wherein the viability or virulence of the bacteriophage particles in the dry bacteriophage product is substantially maintained.

2. The method of claim 1, wherein subjecting comprises subjecting the bulk liquid bacteriophage product comprising a number of viable bacteriophage particles and at least one of a fermentation medium, a lysate, and a host bacteria to the pulse combustion drying.

3. The method of claim 1, further comprising:

introducing a carrier material into the bulk liquid to increase a solids content of the bulk liquid bacteriophage product, wherein subjecting comprises subjecting the bulk liquid bacteriophage product comprising a number of viable bacteriophage particles and the carrier material to the pulse combustion drying.

4. The method of claim 3, wherein introducing the carrier material comprises adjusting a solids content of the bulk liquid bacteriophage product to at least about 20%.

5. The method of claim 3, wherein introducing the carrier material comprises introducing at least one of dried milk, trehalose, and maltodextrin into the bulk liquid bacteriophage product.

6. The method of claim 1, wherein subjecting comprises subjecting the bulk liquid bacteriophage product comprising a number of viable bacteriophage particles to a maximum pressure of about 0.1 bar.

7. The method of claim 1, wherein subjecting comprises subjecting the bulk liquid bacteriophage product comprising a number of viable bacteriophage particles to a contact temperature of about 540° C. or less.

8. The method of claim 1, wherein subjecting the bulk liquid bacteriophage product comprising a number of viable bacteriophage particles to the pulse combustion drying to form a dry bacteriophage product in which the viability or virulence of the bacteriophage particles is substantially maintained results in, at most, a one log reduction in a number of the viable or virulent bacteriophage particles from the bulk liquid bacteriophage product to a dry bacteriophage product.

9. The method of claim 8, wherein subjecting the bulk liquid bacteriophage product comprising a number of viable bacteriophage particles to the pulse combustion drying to form a dry bacteriophage product in which the viability or virulence of the bacteriophage particles is substantially maintained results in, at most, reduction of about 25% in a number of the viable or virulent bacteriophage particles from the bulk liquid bacteriophage product to a dry bacteriophage product.

10. The method of claim 1, wherein the pulse combustion drying is effected at a rate of about one liter every ninety seconds or faster.

11. The method of claim 3, wherein introducing the carrier material comprises introducing a solid carrier material into the bulk liquid.

12. A method for manufacturing a dry bacteriophage preparation, comprising:

providing a bulk liquid bacteriophage product comprising a number of viable bacteriophage particles;

adding a carrier material in dry form to the bulk liquid bacteriophage product to increase a solids content of the bulk liquid bacteriophage product; and subjecting the bulk liquid bacteriophage product to a pulse combustion drying process to form a dry bacteriophage product, wherein the viability or virulence of the bacteriophage particles in the dry bacteriophage product is substantially maintained.

13. The method of claim 12, wherein subjecting comprises subjecting the bulk liquid bacteriophage product comprising a number of viable bacteriophage particles and at least one of a fermentation medium, a lysate, and a host bacteria to the pulse combustion drying process.

14. The method of claim 12, wherein subjecting comprises subjecting the bulk liquid bacteriophage particles and product comprising a number of viable the carrier material to the pulse combustion drying process.

15. The method of claim 14, wherein introducing the carrier material comprises adjusting a solids content of the bulk liquid bacteriophage product to at least about 20%.

16. The method of claim 14, wherein introducing the carrier material comprises introducing at least one of dried milk, trehalose, and maltodextrin into the bulk liquid bacteriophage product.

17. The method of claim 12, wherein subjecting comprises subjecting the bulk liquid bacteriophage product comprising a number of viable bacteriophage particles to a maximum pressure of about 0.1 bar.

18. The method of claim 12, wherein subjecting comprises subjecting the bulk liquid bacteriophage product comprising a number of viable bacteriophage particles to a contact temperature of about 540° C. or less.

19. The method of claim 12, wherein subjecting the bulk liquid bacteriophage product comprising a number of viable bacteriophage particles to form a dry bacteriophage product in which the viability or virulence of the bacteriophage particles is substantially maintained to the pulse combustion drying process comprising a number of viable bacteriophage particles to form a dry bacteriophage product in which the viability or virulence of the bacteriophage particles is substantially maintained results in, at most, a one log reduction in the number of viable or virulent bacteriophage particles from the bulk liquid bacteriophage product to a dry bacteriophage product.

20. The method of claim 19, wherein subjecting the bulk liquid bacteriophage product comprising a number of viable bacteriophage particles to form a dry bacteriophage product in which the viability or virulence of the bacteriophage particles is substantially maintained to the pulse combustion drying comprising a number of viable bacteriophage particles to form a dry bacteriophage product in which the viability or virulence of the bacteriophage particles is substantially maintained results in, at most, reduction of about 25% in a number of viable or virulent bacteriophage particles from the bulk liquid bacteriophage product to a dry bacteriophage product.

21. The method of claim 12, wherein the pulse combustion drying process is effected at a rate of about one liter every ninety seconds or faster.

\* \* \* \* \*